United States Patent [19]

Scholz et al.

[11] 4,126,748

[45] Nov. 21, 1978

[54] PROCESS FOR THE PRODUCTION OF CARBOXYLIC ACID ESTERS BY CATALYTIC OXIDATION OF ALCOHOLS

[75] Inventors: Bernhard Scholz; Fritz Obenaus; Gerhard Franz; Hans-Jürgen Erberich; Heinz-Otto Reitemeyer, all of Marl, Fed. Rep. of Germany

[73] Assignee: Chemische Werke Huels, A.G., Fed. Rep. of Germany

[21] Appl. No.: 781,391

[22] Filed: Mar. 25, 1977

[30] Foreign Application Priority Data

Apr. 17, 1976 [DE] Fed. Rep. of Germany ....... 2616979

[51] Int. Cl.$^2$ .............................................. C07C 67/40
[52] U.S. Cl. ................................ 560/239; 260/603 C; 562/538; 568/594
[58] Field of Search ......................... 260/495; 560/239

[56] References Cited

U.S. PATENT DOCUMENTS 2,287,803  6/1942  Hull .................................... 260/495

Primary Examiner—Vivian Garner
Attorney, Agent, or Firm—Millen & White

[57] ABSTRACT

In an improved process for the production of carboxylic acid esters by catalytic oxidation of alcohols in the liquid phase, primary alcohols of 1–4 carbon atoms are oxidized with molecular oxygen at temperatures of about 100°–250° C. in the presence of catalytic amounts of a compound of Co, Mn, Cr, or Fe, and an acid having a first dissociation constant $K_1$ greater than $10^{-3}$, dissolved in the reaction mixture.

10 Claims, No Drawings

PROCESS FOR THE PRODUCTION OF CARBOXYLIC ACID ESTERS BY CATALYTIC OXIDATION OF ALCOHOLS

BACKGROUND OF THE INVENTION

U.S. Pat. No. 3,257,448 discloses producing carboxylic acid esters by liquid phase oxidation of a mixture of an alcohol and an aldehyde, using a mixture of palladium chloride and copper chloride as catalyst. Large amounts of lithium salts are required as binding agent for the water thus produced. The catalyst system is very complex and difficult to handle.

U.S. Pat. No. 3,639,449 discloses a process by which alcohols or mixtures of alcohols and aldehydes are oxidized to esters in the liquid or gaseous phase at an elevated temperature by molecular oxygen in the presence of heterogeneous noble metal catalysts. Activated carbon and diatomaceous earth are used as support material when the reaction is done in the liquid phase. Since noble metal catalysts are expensive and the catalysts undergo loss of metal during use owing to mechanical abrasion, the losses are of great economic significance. In a subsequent publication, Chem., Abs, vol. 79 (1973):4594a, the inventor of U.S. Pat. No. 3,639,449, reported that, in the liquid phase, aldehydes inactivate the catalyst because of their strong affinity for the catalyst. Because aldehydes are produced in all cases of oxidation of alcohols, such a catalyst can not be used over a prolonged period of time.

It is an object of the present invention to provide a process using an inexpensive and effective catalyst system, which is not affected by catalyst abrasion.

SUMMARY OF THE INVENTION

This invention relates, in a process for the production of carboxylic acid esters by catalytic oxidation of alcohols in the liquid phase of a primary straight chain alcohol or a mixture of an aldehyde and a primary straight chain alcohol, each of 1-4 carbon atoms, with molecular oxygen at elevated temperatures in the presence of an oxidation catalyst, to the improvement which comprises employing as catalyst a solution in the liquid phase of (a) a compound of Co, Mn, Cr, or Fe, and (b) an acid having a first dissociation constant $K_1$ greater than $10^{-3}$.

DETAILED DESCRIPTION

The reaction takes place according to the equation

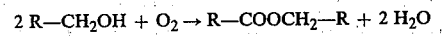

$$2\ R\text{---}CH_2OH + O_2 \rightarrow R\text{---}COOCH_2\text{---}R + 2\ H_2O$$

Suitable alcohols for the process are methanol, ethanol, n-propanol, and n-butanol. Methyl formate is produced from methanol, ethyl acetate from ethanol, etc. When a mixture of alcohols is used, a mixture of the corresponding esters is obtained. Thus, methyl formate, methyl acetate, ethyl formate, and ethyl acetate are produced from a mixture of methanol and ethanol. The proportions of the thus-formed esters can vary with the reaction conditions.

It is also possible to employ a mixture of an alcohol and an aldehyde.

A combination of a metal compound and an acid is utilized as catalyst, which is homogeneously dissolved in the reaction system. Suitable metal compounds are any compound of Mn, Co, Cr, Fe which is sufficiently soluble in the reaction system. The lower limit of solubility for the practice of this invention is 0.2 p.p.m. but compounds having a solubility above 1 000 p.p.m. are preferred.

Suitable metal compounds include salts, wherein the metal is present either as the anion or as the cation, metal complexes, and other metal compounds, e.g., oxides. Acetates, naphthanates, or acetylacetone complexes are preferred, especially the naphthenates and acetates, but good results are also obtained with sulfates, nitrates, chlorides, oxides, chromates, etc. Mixtures of two or more metal compounds are also suitable as catalysts.

Acids which can be employed are those having a first dissociation constant greater than about $10^{-3}$, for example, inorganic acids, including HCl, $HNO_3$, $HClO_4$, $H_2SO_4$, HBr, $H_3PO_4$, HI, etc,; organic acids such as methanesulfonic acid, p-chlorobenzoic acid, oxalic acid, trichloracetic acid, etc.

The acid component can be formed in situ from compounds which are hydrolyzed by the water present in the reaction mixture. For example, $BF_3$ can be added to the reaction mixture to produce HF or $HBF_4$, either of which is effective as a catalyst. For reasons of economy, acids which attack the reactor material only to a minimum extent will be employed. Especially preferred are phosphoric and sulfuric acids, but satisfactory results are also achieved with oxalic and trichloroacetic acids. Mixtures of acids can be used.

The metal compounds are catalytically active in extremely minor amounts. Usually, a concentration of 0.2-100 p.p.m., calculated as the metal, is employed, based on the amount by weight of the alcohol used. At metal concentrations below 0.2 p.p.m., catalytic activity begins to decrease. Above a concentration of 100 p.p.m., no additional improvement can be detected. Concentrations between 1 and 10 p.p.m. are most preferred from a technical process viewpoint. Sometimes metal salts are present in the reactor owing to corrosion of the reactor material, even in vessels made of stainless steel, in amounts sufficiently high to have catalytic activity.

The acid concentration in the reaction mixture should be above about 5 p.p.m., based on the amount by weight of alcohol employed. Below this concentration catalytic activity decreases. At acid concentrations above 100 p.p.m., an impairment of catalytic effect is often observed. However, phosphoric acid can be utilized at levels higher than 100 p.p.m., although an increase in phosphoric acid concentration about 100 p.p.m. does not give improved results. A range of about 5-100 p.p.m. by weight of alcohol can be utilized. In general, a range of 50-100 p.p.m. is maintained under technical conditions.

If necessary, in view of the low concentrations, the catalyst can be separated from the reaction product by precipitation and filtration or, preferably, by ion exchange.

A suitable oxidizing agent is molecular oxygen in the form of oxygen, air or mixtures of oxygen and nitrogen. It is also possible to use oxygen mixed with other gases which are inert under the reaction conditions. The use of air is especially simple and economical.

The reaction is generally conducted at temperatures between 50° and 250° C. Below 50° C., the reaction rate is very low, whereas above 250° C., further oxidation of alcohols to $CO_2$, CO and $H_2O$ increases very markedly. Preferably, a temperature range of 100°-200° C. is utilized, since a high reaction rate is obtained with concomitantly relatively low by-product formation. Since the reaction takes place in the liquid phase, the pressure employed must be the same as or greater than the vapor pressure of the alcohol being used at the reaction temperature selected, in order to maintain the liquid phase.

In a most preferred embodiment of the process, the compound of Co, Mn, Cr or Fe is an acetate or naphthenate; the acid is phosphoric or sulfuric acid; the compound of Co, Mn, Cr or Fe is utilized in a concentration of about 1–10 p.p.m. by weight of the alcohol; the acid is employed in a concentration of 50—100 p.p.m. by weight of the alcohol and the temperature is 100°–200° C.

Oxidative esterification of alcohols can be effected discontinuously or continuously. Under commercial conditions, the operation is generally conducted continuously. Suitable reactors are those customary for gas-liquid reactions, for example, bubble column reactors.

The reaction time for the oxidative esterification is ordinarily between 1.5 and 15 hours. Conversion of the alcohol increases with longer reaction time, but, with a longer oxidation time, the amount of dissociation products such as $CO_2$, CO, $CH_4$, and $H_2O$, also increases. If the liquid and gaseous phases are mixed particularly intimately, the reaction time can be substantially shorter. Occasionally a certain time passes before the reaction starts, that is, there is an induction period. When phosphoric acid is the acid component, the induction period is extraordinarily brief. It is recommended that the reaction be initiated using phosphoric acid or by adding a minor amount of phosphoric acid to the reaction mixture.

Corresponding aldehydes, acetals, and carboxylic acids are produced as by-products of the oxidative esterification. In a continuous process, by-products are recycled to the reaction mixture, after separation from the thus-formed ester, e.g., by distillation. In a batch mode of operation the by-products are added to a new reaction batch, insofar as the by-products are not utilized in some other way. The final result is that only water and minor quantities of CO, $CO_2$, and $CH_4$ are obtained in addition to the desired ester.

If the ester formed by the reaction has a lower boiling point than the starting alcohol, it is advantageous to remove the thus-produced ester continuously from the reaction mixture by distillation. Hydrolysis of the ester product by water of reaction can thus be limited to a minor amount. In producing methyl formate, production of strongly corrosive formic acid can be repressed in this way.

The catalyst of this invention has good selectivity with short reaction times and a very low proportion of total oxidation to CO and $CO_2$. The catalyst components are quite inexpensive and moreover are utilized in extremely low concentrations. No inhibition of the catalyst activity by reaction products occurs. Even at water content above 10% in the reaction mixture, the reaction takes place at a satisfactory rate, and high conversions are attainable without lowering selectivity, thus making it possible to conduct the process in an economical manner.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degree Celsius; unless otherwise indicated, all parts and percentages are by weight.

EXAMPLES 1–17 AND 21–27

Methanol and ethanol, respectively were oxidized in a reactor equipped with a reflux condenser and consisting of a nickel-chromium-molybdenum alloy ("HASTELLOY C"). The reactor was gold-electroplated on the inside to avoid corrosion. In each run, 230 g. of the alcohol, a metal compound and an acid, were charged into the reactor. The latter was heated to the reaction temperature, and air was then introduced as the oxidizing agent. After initiation of the reaction, fresh methanol with catalyst dissolved therein was continuously added and the corresponding amount of reaction product was withdrawn continuously. The feed rate was chosen so that a specific average residence time for the methanol in the reactor was obtained. In batch experiments, no fresh methanol was added, but the experiment was terminated after a certain reaction time. The catalyst concentration in the reactor was monitored by analyses. The liquid reaction product withdrawn from the reactor, along with the escaping waste gas, was analyzed by gas chromatography and the catalyst concentration was analyzed by photometrical methods (metal compound) resp. titration (acid compound). The results obtained with differing values of variables are compiled in the table.

EXAMPLES 18–20

In a bubble column reactor made of glass and equipped with a reflux condenser and a water trap device for removing the water from the cycle, 150 g. of n-butanol was combined with catalytic amounts of a metal compound and an acid. After reaching the reaction temperature, air was introduced as the oxidizing agent. The results are summarized in the table.

TABLE

| Example | Alcohol | Temp. (°C) | Pressure (bar) | Amount of Air (Nl./h.) | Catalyst Metal Compound (p.p.m. Metal) | Catalyst Acid (p.p.m.) | Residence Time, Reaction Time (h.) | Conversion (% by Wt.) | Yield, Based on Conversion (%) Ester | Yield Acetal | Yield Aldehyde | Yield Acid | +CH₄ CO + CO₂ |
|---|---|---|---|---|---|---|---|---|---|---|---|---|---|
| 1 | CH₃OH | 150 | 18 | 70 | 2.5 Co(II)acetate | 100 H₃PO₄ | 3.5 | 28.7 | 57.5 | 37.8 | 1.8 | 1.5 | 1.4 |
| 2 | CH₃OH | 150 | 18 | 70 | 100 Mn(II)acetate | 680 H₃PO₄ | 5 (disc.) | 40.0 | 50.9 | 34.9 | 1.1 | 1.4 | 1.5 |
| 3 | CH₃OH | 160 | 23 | 70 | 3 Cr(III)acetylacetonate | 100 H₂SO₄ | 3.5 | 44.8 | 51.0 | 42.3 | 1.9 | 1.7 | 3.1 |
| 4 | CH₃OH | 150 | 18 | 70 | 3.5 Fe(III)acetylacetonate | 100 H₃PO₄ | 3.6 | 45.3 | 58.0 | 38.6 | 0.7 | 0.7 | 2.0 |
| 5 | CH₃OH | 150 | 18 | 70 | 50 Co(II)+2.5 Mn(II)acetate | 680 H₃PO₄ | 4.3 | 35.2 | 55.9 | 42.2 | 1.3 | 0.1 | 1.5 |
| 6 | CH₃OH | 160 | 23 | 70 | 2 Co(II)acetate | 100 Oxalic Acid | 2.3 | 35.2 | 51.7 | 45.1 | 1.9 | 1.4 | 1.4 |
| 7 | CH₃OH | 160 | 23 | 70 | 4 Co(II)acetate | 40 CCl₃COOH | 3.1 | 33.8 | 58.6 | 35.4 | 1.7 | 0.9 | 3.4 |
| 8 | CH₃OH | 150 | 18 | 70 | 2 Co(II)acetate | 50 H₃PO₄ | 1.9 | 21.1[1] | 47.6 | 47.4 | 2.8 | 0 | 2.2[2] |
| 9 | CH₃OH | 150 | 18 | 70 | 2 Co(II)acetate | 50 H₃PO₄ | 2.0 | 23.1[1] | 92.2 | — | 3.9 | 0 | 3.9[3] |
| 10 | CH₃OH | 150 | 18 | 70 | 100 Co(II) naphthenate | 680 H₃PO₄ | 3.5(disc.) | 43.6 | 53.5 | 43.1 | 1.4 | 0.4 | 1.6 |
| 11 | CH₃OH | 170 | 25 | 105 | 3.5 Fe(III)+3.5 Co(III)acetylacetonate | 100 H₃PO₄ | 2.6 | 60.2 | 70.8 | 25.7 | 0.6 | 0.9 | 2.0 |
| 12 | C₂H₅OH | 145 | 14 | 40 | 5 Co(III)acetylacetonate | — | 10(disc.) | 0 | | | | | [4] |
| 13 | C₂H₅OH | 145 | 14 | 40 | 10 Co(II)acetate | 11000 H₃PO₄ | 10(disc.) | 0 | | | | | [4] |
| 14 | C₂H₅OH | 120 | 6.6 | 50 | 8 Co(II)acetate | 100 H₃PO₄ | 7(disc.) | 65 | 30 | 22 | 21 | 15 | 11 |
| 15 | C₂H₅OH | 120 | 6.6 | 75 | | 4500 H₃PO₄ | 6 (disc.) | 58 | 34 | 24 | 22 | 11 | 9 |
| 16 | C₂H₅OH | 145 | 15 | 40 | 50 Co(II)acetate | 90 H₂SO₄ | 10 (disc.) | 90 | 32 | 2 | 12 | 45 | 9 |
| 17 | C₂H₅OH | 145 | 14 | 40 | 100 Co(II)acetate | 11000 H₃PO₄ | 7 (disc.) | 60 | 55 | 10 | 10 | 17 | 7 |
| 18 | C₄H₉OH | 109 | 1 | 15 | 60 Co(II)acetylacetonate | 600 H₃PO₄ | 5 (disc.) | 14 | 82 | 9 | 4 | 3 | 2 |
| 19 | C₄H₉OH | 109 | 1 | 15 | 150 Cr(III)acetylacetonate | 700 H₃PO₄ | 9 (disc.) | 23 | 24 | 21 | 36 | 5 | 3 |
| 20 | C₄H₉OH | 108 | 1 | 15 | 150 Co(III)acetylacetonate | 1200 H₃PO₄ | 35 (disc.) | 79 | 59 | 1 | 1 | 16 | 8 |
| 21 | CH₃OH | 145 | 18 | 70 | 3 Cr(VI) oxide | 100 H₃PO₄ | 2.6 | 36.5 | 47.7 | 46.6 | 3.4 | 1.2 | 1.1 |
| 22 | CH₃OH | 160 | 23 | 43 | 3 Na₂Cr₂O₇ | 100 H₃PO₄ | 2.8 | 48.1 | 66.1 | 28.5 | 0.9 | 1.7 | 2.8 |
| 23 | CH₃OH | 160 | 23 | 43 | 4 Fe(III)chloride | 100 H₃PO₄ | 2.3 | 29.3 | 47.9 | 44.6 | 1.4 | 1.7 | 4.4 |
| 24 | CH₃OH | 150 | 18 | 70 | 2 Co(II)acetate | 6 H₃PO₄ | 3.5 | 24.3[1] | 41.4 | 55.8 | 2.3 | 0.4 | 1.6 |
| 25 | CH₃OH | 160 | 23 | 70 | 0.4 Co(II)acetate 0.1 Fe(III)acetylacetone 0.2 Cr(III)acetylacetone | 76 H₃PO₄ | 2.5 | 31.6[1] | 92.0 | — | 2.2 | 2.8 | 3.0[5] |
| 26 | CH₃OH | 160 | 23 | 70 | 2 Co(II)acetate 1 Cr(III)acetylacetonate | 100 H₃PO₄ | 2.4 | 33.2[1] | 48.9 | 44.1 | 2.1 | 2.3 | 2.6[6] |
| 27 | CH₃OH | 160 | 23 | 70 | 3 Cr(III)acetylacetonate | 100 BF₃ | 2.2 | 48.2 | 57.6 | 34.0 | 1.4 | 3.7 | 3.3 |

[1] CH₃OH Conversion.
[2] CH₃OH Contains 20% H₂O.
[3] CH₃OH Contains 20% Acetal.
[4] Comparative Experiments.
[5] 12.5% by Weight of Acetal in CH₃OH.
[6] 13% by Weight of Aldehyde + CH₃OH Were Employed.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. In a process for the liquid phase catalyzed oxidation of a primary lower aliphatic alcohol to a carboxylic acid ester with molecular oxygen at elevated temperatures and in the presence of an oxidation catalyst, the improvement which comprises employing methanol as the alcohol and employing as the oxidation catalyst a solution in the methanol of (a) a compound of Co, Mn, Cr or Fe and (b) an acid having a first dissociation constant $K_1$ greater than $10^{-3}$, in an amount of at least about 5 p.p.m. by weight based on the methanol.

2. The process of claim 1, wherein the compound of Co, Mn, Cr or Fe is employed in an amount of 0.2–100 p.p.m. of metal by weight of the methanol.

3. The process of claim 1, wherein the compound of Co, Mn, Cr or Fe is employed in an amount of 1–10 p.p.m. of metal by weight of the methanol.

4. The process of claim 1, wherein the acid is employed in an amount of about 5–100 p.p.m. by weight of the methanol.

5. The process of claim 1, wherein the acid is employed in an amount of about 50–100 p.p.m. by weight of the methanol.

6. The process of claim 1, wherein the temperature is about 100°–200° C.

7. The process of claim 1, wherein the compound of Co, Mn, Cr or Fe is an acetate or naphthenate.

8. The process of claim 1, wherein the oxidation is initiated with phosphoric acid.

9. The process of claim 1, wherein the compound of Co, Mn, Cr or Fe is an acetate or naphthenate and is employed in a concentration of about 1–10 p.p.m. by weight of the methanol, the acid is phosphoric or sulfuric acid and is employed in a concentration of 50–100 p.p.m. by weight of the methanol and the temperature is 100°–200° C.

10. The process of claim 1 wherein the liquid phase contains an aldehyde.

* * * * *